(12) United States Patent
Vernon

(10) Patent No.: US 11,232,865 B2
(45) Date of Patent: *Jan. 25, 2022

(54) REMOTE COMMUNICATION PORTAL, SYSTEM AND METHOD OF USE

(71) Applicant: My Virtual Exam, Inc., Delray, FL (US)

(72) Inventor: Shawn Vernon, Delray, FL (US)

(73) Assignee: MY VIRTUAL EXAM, INC., Delray, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/181,807

(22) Filed: Feb. 22, 2021

(65) Prior Publication Data

US 2021/0202087 A1 Jul. 1, 2021

Related U.S. Application Data

(63) Continuation of application No. 16/822,266, filed on Mar. 18, 2020, now Pat. No. 11,043,303.

(60) Provisional application No. 62/819,916, filed on Mar. 18, 2019.

(51) Int. Cl.
*G16H 80/00* (2018.01)
*G16H 40/67* (2018.01)
*H04N 7/14* (2006.01)

(52) U.S. Cl.
CPC .......... *G16H 40/67* (2018.01); *G16H 80/00* (2018.01); *H04N 7/147* (2013.01)

(58) Field of Classification Search
CPC ........ G16H 40/63; G16H 80/00; G16H 40/67; H04N 7/14; H04N 7/144; H04N 7/147
USPC .......................................... 348/14.01–14.16
See application file for complete search history.

(56) References Cited

U.S. PATENT DOCUMENTS

| | | | |
|---|---|---|---|
| 2016/0302666 A1* | 10/2016 | Shaya | H04L 65/403 |
| 2017/0098051 A1* | 4/2017 | Balram | G16H 70/20 |
| 2018/0160907 A1* | 6/2018 | Verma | A61B 7/00 |
| 2018/0247029 A1* | 8/2018 | Fish | G16H 15/00 |
| 2018/0268109 A1* | 9/2018 | Ramgir | A61B 8/565 |
| 2018/0301219 A1* | 10/2018 | Sanford | G16H 40/67 |
| 2019/0254903 A1* | 8/2019 | Hag | A61B 90/37 |

* cited by examiner

*Primary Examiner* — Melur Ramakrishnaiah
(74) *Attorney, Agent, or Firm* — William Gray Mitchell

(57) ABSTRACT

The invention is a remote electronic communication system and method of use, providing means of real-time, full-body video and audio while a variety of sensors or measurement devices read and communicate electronic data to one or all participants.

14 Claims, 9 Drawing Sheets

REMOTE COMMUNICATION PORTAL, SYSTEM AND METHOD OF USE

CROSS REFERENCE TO RELATED APPLICATIONS

This application claims priority to U.S. application Ser. No. 16/822,266, filed Mar. 18, 2020, and thence to U.S. provisional application 62/819,916, filed Mar. 18, 2019.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

SEQUENCE LISTING INCLUDED AND INCORPORATED BY REFERENCE HEREIN

Not applicable.

BACKGROUND

Field of the Invention

The invention is a remote communication portal system and method of use.

Background of the Invention

The US spends $3.2 trillion of its annual gross domestic product (GDP) on health. Unnecessary care services add up to an estimated $750 billion in wasteful health care spending each year, according to the National Academy of Sciences.

At the same time, the medical profession faces rising operational costs that are a threat to profitability, while rural communities cannot attract physicians willing to live in remote, sparsely populated areas. At present, there are only 68 primary care doctors per 100,000 people in rural areas, compared to 84 such doctors in urban areas. Even in urban and suburban areas, there are often an insufficient number of primary care physicians to treat the population, especially the uninsured, meaning that many patients with low-level issues must resort to urgent care or emergency room visits rather than wait days for an appointment, or forego medical treatment altogether.

The lack of doctors in much of the U.S. adversely affects both the availability and responsiveness of medical care and treatment, leading to undiagnosed and untreated afflictions that adversely affect the health and quality of life of the population, with untreated low-level issues often leading to more serious costly problems down the road.

There are 10,000 urgent care locations in the U.S. and 160 million people visit urgent care offices annually, with many more making unnecessary emergency room visits. When patients use urgent care or ERs for low-cost, low-risk and high-volume services, such as ear and sinus infections, sore throats, flu and rashes, these visits result in higher costs for both patient and insurer, and waste valuable time for emergency medical teams that should be focusing on patients with more serious issues.

Remote portals for examination and diagnosis become even more attractive in the context of epidemics. Such portals are perfectly suited for examinations of potentially contagious patients, without forcing such patients into close contact with other patients or providers, thus mitigating against the further spread of communicable disease.

There exists a need for a system connecting patients to available medical care professionals outside the patients' immediate geographic area, allowing for timely examination, diagnosis and treatment of conditions when a live, in-person examination cannot occur for reasons of unavailability.

The invention as disclosed herein addresses this problem by providing a portal system wherein patients may make appointments on a near-term or same-day basis and access a wide network of available medical care professionals throughout the country, utilizing telecommunications and medical sensory technology.

BRIEF SUMMARY OF THE INVENTION

In a preferred embodiment, a remote communication portal system for two or more participants, comprising an examination portal connected to a mobile device by an intranet or the internet, each such portal comprising at least one of each of a video screen, a microphone, a camera, and an audio speaker, wherein the examination portal comprises one or more sensors and/or measurement devices for the gathering of biometric data, a control unit or central processor unit with a memory and power supply for the gathering and transmission of video, audio and sensor data between the examination portal and mobile device, and the mobile device comprises a means for reviewing and controlling such video, audio and sensor data.

In another preferred embodiment, the examination portal as described herein, wherein the sensors and/or measurement devices include, without limitation, one or more of the following:

1. GSR Sensor—Galvanic Skin Response, used to measure the electrical conductance of the skin.
2. Airflow Sensor—Used to measure the breathing rate in a patient.
3. ECG Sensor—Electrocardiography, used to assess the electrical and muscular functions of the heart.
4. EMG Sensor—Electromyography, used to measure the electrical activity of muscles.
5. Temperature Sensor—Used to monitor a patient's skin surface temperature.
6. Body Position Sensor—Used to diagnose sleep-disordered breathing.
7. Snore Sensor—This sensor attaches to the neck and records vibration
8. Sound Generator
9. Alert Patient Button
10. Spirometer—Used to measure the volume of air inspired and expired by the lungs.
11. Glucometer Meter—Used to check blood sugar levels.
12. SPO2 Pulsioximeter—Used to measure oxygen levels of the blood
13. SPO2 Pulsioximeter BLE—Used to measure oxygen levels of the blood
14. Blood Pressure Sensor (sphygmomanometer)
15. Blood Pressure BLE
16. Scale
17. Alarm Button
18. Thermal imaging to determine body temperature and/or sites of infection 19. Stethoscope, otoscope, opthalmoscope, nasal speculum,
20. Weight scale and height measuring sensor
21. Tonometer
22. Slit lamp
23. Ophthalmoscope
24. Thermometer
25. Reflex hammer
26. Tongue depressor In another preferred embodiment, the examination portal as described herein, wherein the examination portal is used by a medical patient and the mobile device is used by a medical professional.

In another preferred embodiment, the examination portal as described herein, wherein the examination portal comprises one or more automatic biosanitation cleaning features from the group including but not limited to, an ozone generator, a misting system including one or more misters, a reservoir and pump(s), and one or more UVC lamp.

In another preferred embodiment, the examination portal as described herein, further comprising one or more telecommunication security protocols, including but not limited to Virtual Private Network protocols such as WireGuard® and embedded computer systems controlled by real-time operating systems (RTOS), or other comparable security features.

In another preferred embodiment, the examination portal as described herein, further comprising one or more telecommunication-related algorithms or software such as high-efficiency video coding (HEVC), open-source software such as Arch Linux, a network control protocol such as Real Time Streaming Protocol (RTSP), Screen Overlay for displaying sensor and measurement readings or other data generated for concurrent review by one or more parties to a communication, and, optionally, onsite radio communications such as Bluetooth, BLE Bluetooth Low Energy, WiFi, or similar types of transmission technology for connectivity of sensors and measuring devices.

In another preferred embodiment, the examination portal as described herein, wherein the sensor and/or measurement devices are taken from the group comprising: a CT scan, ultrasound, MRI, PET scan or x-ray machine, or similar radiological device In another preferred embodiment, the examination portal as described herein, wherein the data collected by the sensor and/or measurement devices in the examination portal are visible on the mobile device by means of a screen overlay.

In another preferred embodiment, the medical examination portal as disclosed herein.

In another preferred embodiment, the examination portal as described herein, wherein the portal is self-contained inside an acrylic or similarly durable and transparent box, with at least one LED light strip located on the front of the transparent box and a plurality of wheels on the bottom of such box, wherein such box contains a Bluetooth sensor connected to one or more medical sensors, a motorized, adjustable gear rack comprising at least one camera and a CPU.

In another preferred embodiment, the examination portal as described herein, further comprising a video screen showing a medical patient a data overlay and/or image of a medical professional examining the patient.

In another preferred embodiment, a method of conducting a medical examination on a human patient utilizing the remote communication portal system as described herein.

In another preferred embodiment, the method described herein, wherein the mobile device comprises software employing a control means, whereby the medical professional may manipulate the camera, lights and microphone in the examination portal in real time via radio buttons or similar control means.

In another preferred embodiment, the method described herein, wherein the medical professional may use the control means to manipulate the sensors and/or measurement devices in the examination portal in real time via radio buttons, voice activation, automation in combination with commercially available artificial intelligence plugins or similar control means.

DETAILED DESCRIPTION OF THE INVENTION

Figure 1:
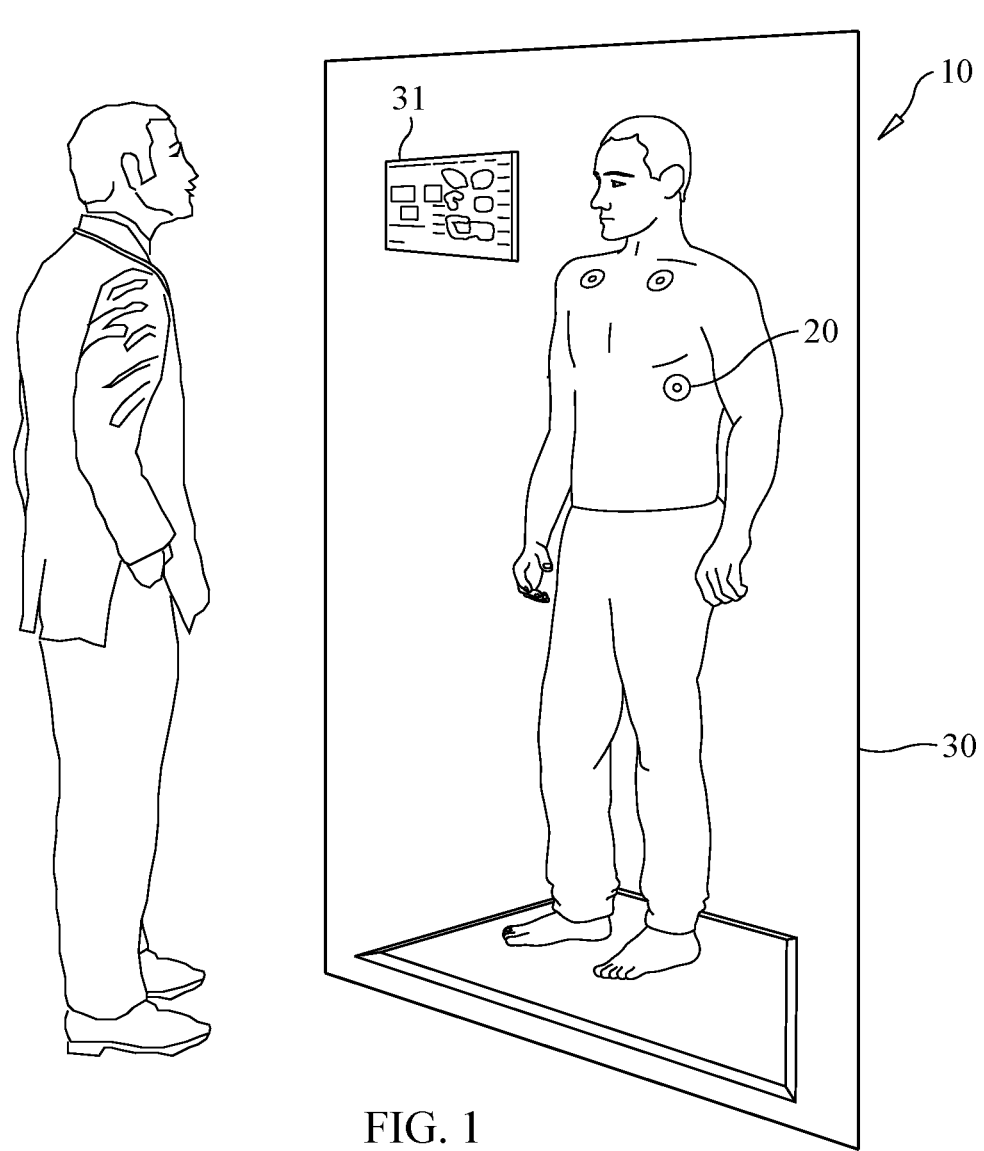
FIG. 1 is a photograph showing a doctor remotely examining a patient in an examination portal.

The invention is a telecommunications portal system (each referred to herein as a My Virtual Exam or MVE Office Portal) embodied as a room wherein a patient can be examined by a doctor. The room contains a plexiglass panel taken from many potential sizes, with a preferred embodiment of approximately 85 inches×49 inches, allowing for viewing a full-sized adult human body in its entirety. The effect is as if the medical professional and patient are sharing the same identical space.

Each panel will be accompanied by one or more cameras, lights and microphones sufficient to allow an examining physician to adequately see and hear the patient during examination, as well as to determine that sensors or similar devices are attached and positioned correctly for proper readings.

The doctor or other medical professional attending the patient will have a similar panel, which is synched with the patient's panel and all sensors or dongles operating in the patient's portal. Such medical professional's panel will require only a power supply and connection via internet or intranet such that it can be located either in an office site or in the doctor's home. The medical professional will simultaneously and/or alternatively have access to a mobile or computer device such as a smartphone, desktop, laptop or tablet for manipulating sensors and cameras, making notes, reading data and drafting written communications, and also for viewing the patient.

In an alternate embodiment, the second portal or panel used by the doctor or medical professional will instead be represented as one or more internet-connectable mobile devices such as a smartphone, tablet, laptop, mountable smart screen or similar mechanism. Such mobile device will comprise all standard components, including but not limited to a memory, processor, screen, camera, microphone, speaker, etc., and will enable a medical professional to conduct remote physical examinations from multiple locations using the same mobile device. In one embodiment, the second portal may comprise two mobile devices such as a phone and mounted screen or computer, acting in combination.

In this iteration, each mobile device will have a memory with appropriate software, ideally embodied as a downloadable application, capable of accessing and displaying photos, video and audio data from the patient as gathered by the first portal, as well as all data generated by the various sensors associated with the first portal. The mobile device will preferably allow the medical professional to communicate verbally and visually with the patient, activate, deactivate and manipulate the patient's examination portal hardware and access the data gathered by such hardware in real time as needed for a given physical examination.

Optionally, the software of the medical professional's mobile device will also allow him or her to combine and compare data generated by two or more sensors simultaneously to aid in making a diagnosis.

MVE portals for patients are self-cleaning and are equipped with multiple sensors or dongles, each attached to a central processing unit, which can be used to monitor more than 20 biometric parameters (vital signs) and which the patient, either by himself or with assistance from an on-site worker, may use to take physical readings. In a preferred embodiment, such sensors will reside in a cabinet with numbered or otherwise marked drawers or cabinets such that the doctor may direct the patient where to access each such sensor and how to use it.

Once the sensor(s) or similar device is in place, the doctor will have nearly instantaneous access to the related readings or information as the sensor communicates its information to the CPU, which transmits the information to the doctor using proprietary data processing and communication software via the internet or an intranet connection. The doctor will have the option of setting the software such that all measured biometric parameters appear on the screen and are visible to both doctor and patient, or are available to the doctor only. Such data optionally can be simultaneously uploaded and saved in memory. In one iteration, the data is saved to the individual doctor's records only. In another iteration, the data is saved into the patient's file in a memory available to the larger network.

Sensors or dongles to be used include but are not limited to any combination of the following:
1. GSR Sensor—Galvanic Skin Response, used to measure the electrical conductance of the skin,
2. Airflow Sensor—Used to measure the breathing rate in a patient,
3. ECG Sensor—Electrocardiography, used to assess the electrical and muscular functions of the heart,
4. EMG Sensor—Electromyography, used to measure the electrical activity of muscles,
5. Temperature Sensor—Used to monitor a patient's skin surface temperature,
6. Body Position Sensor—Used to diagnose sleep-disordered breathing,
7. Snore Sensor—This sensor attaches to the neck and records vibration,
8. Sound Generator,
9. Alert Patient Button,
10. Spirometer—Used to measure the volume of air inspired and expired by the lungs,
11. Glucometer Meter—Used to check blood sugar levels,
12. SPO2 Pulsioximeter—Used to measure oxygen levels of the blood,
13. SPO2 Pulsioximeter BLE—Used to measure oxygen levels of the blood,
14. Blood Pressure Sensor (sphygmomanometer),
15. Blood Pressure BLE,
16. Scale,
17. Alarm Button,
18. Thermal imaging to determine body temperature and/or sites of infection,
19. Stethoscope, otoscope, opthalmoscope, or nasal speculum,
20. Weight scale and height measuring sensor,
21. Tonometer,
22. Slit lamp,
23. Ophthalmoscope,
24. Thermometer,
25. Reflex hammer, and
26. Tongue depressor.

Components of the communications equipment in a given portal unit will include real-time cameras, preferably High Definition (HD) or Ultra High Definition (UHD) quality cameras and monitors, capable of showing full-body pictures but also comprising tilt and zoom controls to allow for up-close examination of specific body areas. An array of cameras may also be provided allowing on medical professional to view the patient front and back, side to side and top and bottom simultaneously as needed, or to create a full 3D body image. In a preferred embodiment, sonar sensors and software will be employed to measure each participant's distance to the screen for automatic adjustment of camera positions, zoom, lighting, microphone sensitivity and/or speaker volume to mimic real-life interaction as closely as possible. An additional embodiment will employ a 99% transparent projection screen of plexiglass or similar material to allow participants to maintain realistic eye contact. In one embodiment, the patient's examination portal will also comprise a video screen visible to the patient wherein the patient may see the examining medical professional and also see the data overlay comprising the patient's vital signs and other data measured by the portal hardware.

Internet or intranet-driven connectivity between portals may comprise one or more telecommunication-related algorithms or software such as high-efficiency video coding (HEVC), open-source software such as Arch Linux, a network control protocol such as Real Time Streaming Protocol (RTSP), Screen Overlay for displaying sensor and measurement readings or other data generated for concurrent review by one or more parties to a communication, and, optionally, onsite radio communications such as Bluetooth, BLE Bluetooth Low Energy, WiFi, or similar types of transmission technology for connectivity of sensors and measuring devices.

A variety of hard and software security measures will be taken to provide complete confidentiality and privacy for the patient and his or her medical information. For on-site security, the portal or site containing portals may employ the use of only wired internet or intranet connections such that no radio transmissions containing patient information emanate. Should radio signal connections be employed, the use of telecommunications additive or multiplicative randomizers (commonly known as "scramblers") may be employed. Communications security features may include Virtual Private Network protocols such as WireGuard®, embedded computer systems controlled by real-time operating systems (RTOS) and other, similar systems. In any event, data security systems shall ensure HIPPA compliance of patient data storage and transfer.

Features of the communications system will be state of the art, including high-efficiency video coding (HEVC), an open-source software such as Arch Linux, a network control protocol such as Real Time Streaming Protocol (RTSP), Screen Overlay for displaying sensor and measurement readings or other data generated for concurrent review by one or more parties to a communication, and, optionally, onsite radio communications such as Bluetooth, BLE Bluetooth Low Energy, WiFi, or similar types of transmission technology for connectivity of sensors and measuring devices.

The disclosed system of simultaneous video, audio, sensory and measurement data will apply to many fields other than medical diagnosis and treatment. Within the field of medicine, the invention may also be applied to the application of radiological and other testing, including MRIs, CT scans, ultrasounds, x-rays, PET scans and other forms of imaging.

During crises involving communicable pathogens, such as the recent coronavirus pandemic, self-cleaning features of each portal will also be invaluable. The use of remote cleaning such as misting nozzles attached via pump to reservoirs of antibacterial and antiviral cleaning products allow the reservoir to be filled without a worker ever entering the portal. Similarly, the use of UVC lights to kill pathogens between uses and a consistently-running ozone generator allow for constant self-cleaning with minimal hands-on contact by staff. Such staff contact can be kept to daily or less, allowing staff to more easily wear full protective gear whenever they do have to enter and handle surfaces inside the portal.

Outside the medical field, the invention may have uses including but not limited to dating services, pharmaceutical dispensaries, instructional training or tutoring, fitness training, lessons in music or other, similar disciplines, as well as job interviewing and corporate training. In short, the invention has the capacity to eliminate the need for persons to physically inhabit the same space for many types of interactions.

DETAILED DESCRIPTION OF THE FIGURES

The figures submitted as a part of this provisional application are each marked directly with part/component identifications. FIG. 1 shows a doctor remotely examining a patient in an examination portal 10. Wired sensors 20 attached to the patient providing an instant data flow for the doctor, appearing on the screen 30 as a screen data overlay 31.

Figure 2:
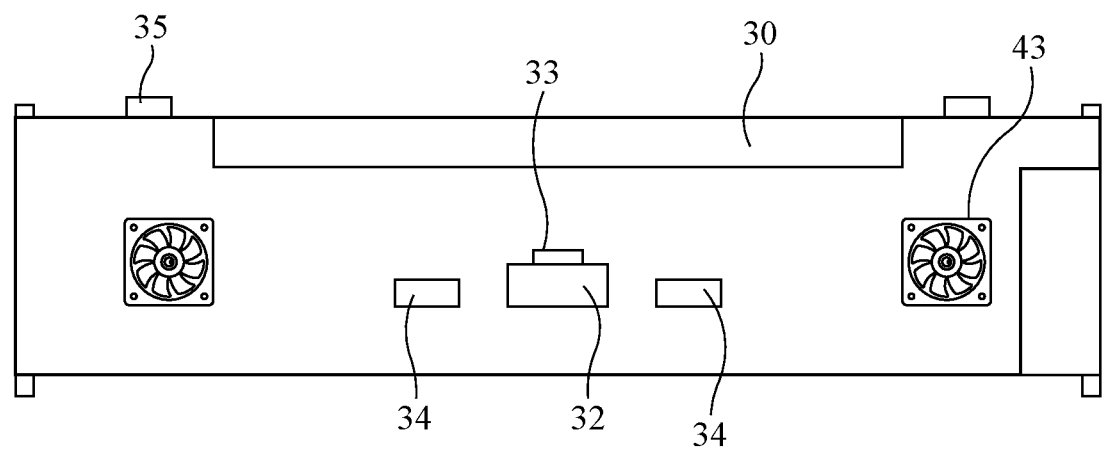
FIG. 2 is a line drawing showing the layout of portal screen, lights, camera, microphone and speakers.

FIG. 2 shows the layout of portal screen 30, with lights 35, camera 32, microphone 33 and speakers 34. In the pictured embodiment, each of the camera, microphone and speakers are located behind a viewing screen 30 of approximately 50-52" in size. The figure notes the use of 8 LED spot lights, with 6 being lit at any given time. Extractor fans are pictured for regularly removing potentially contaminated air. The depth of the entire unit in this embodiment is 21", the entire width is 83", and the screen projector is shown as a gray box in the lower left.

Figure 3:
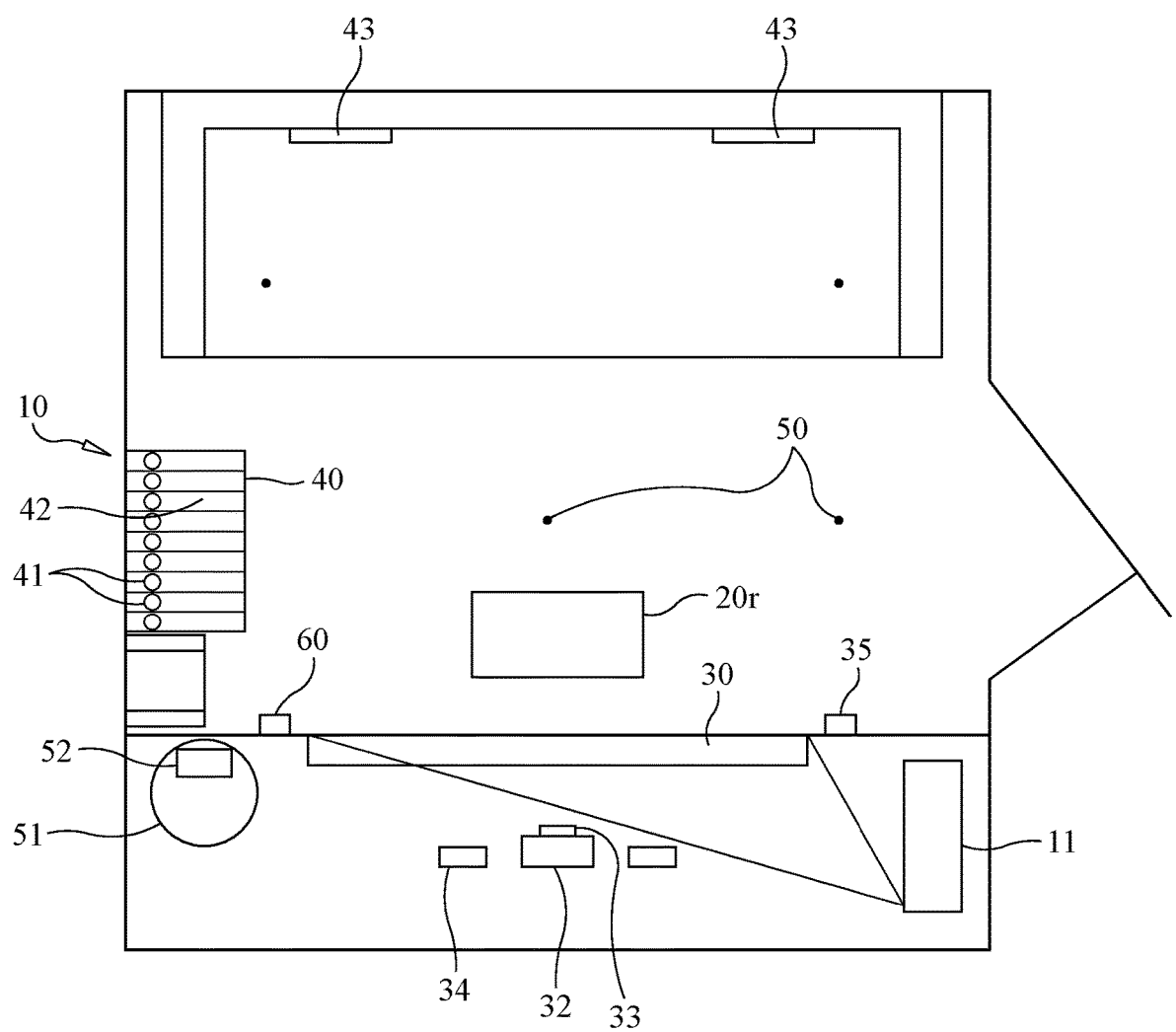
FIG. 3 is a line drawing showing the layout of an off-site examination portal.

FIG. 3 shows the layout of an off-site examination portal 10 with self-cleaning features. This figure shows a cabinet 40 for health sensors including multiple compartments with lids, each comprising a disinfection mechanism utilizing UV-C lamps 41 for cleaning sensors 20 after each use. Misters 50 to spray liquid disinfectant solutions are shown for the larger portal space, drawing from a reservoir 51 and pump system 52. An ozone generator 60 is also shown for purposes of maintaining a germ-free environment. The screen 30 of FIG. 2 is shown in the lower portion, with an optional projector 36, which will not be needed when utilizing LCD display.

Figure 4:
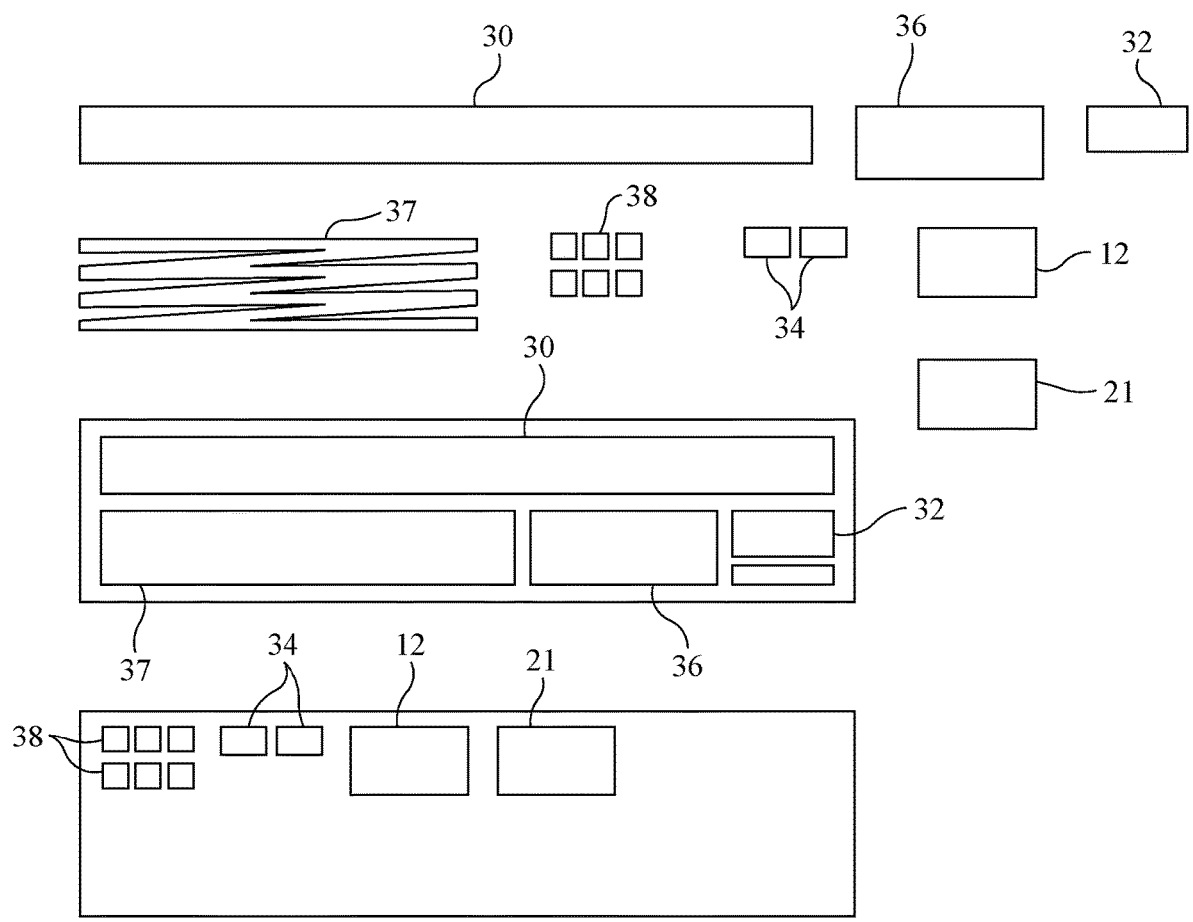
FIG. 4 is a line drawing showing the layout of a mobile examination portal.

FIG. 4 shows the layout of electronic components of a mobile examination portal, including screen 30, frame 37, LED lights 38, speakers 34, projector 36, camera 32, electronics box 12 and sensor box 21. Not pictured are any control unit or CPU.

Figure 5:
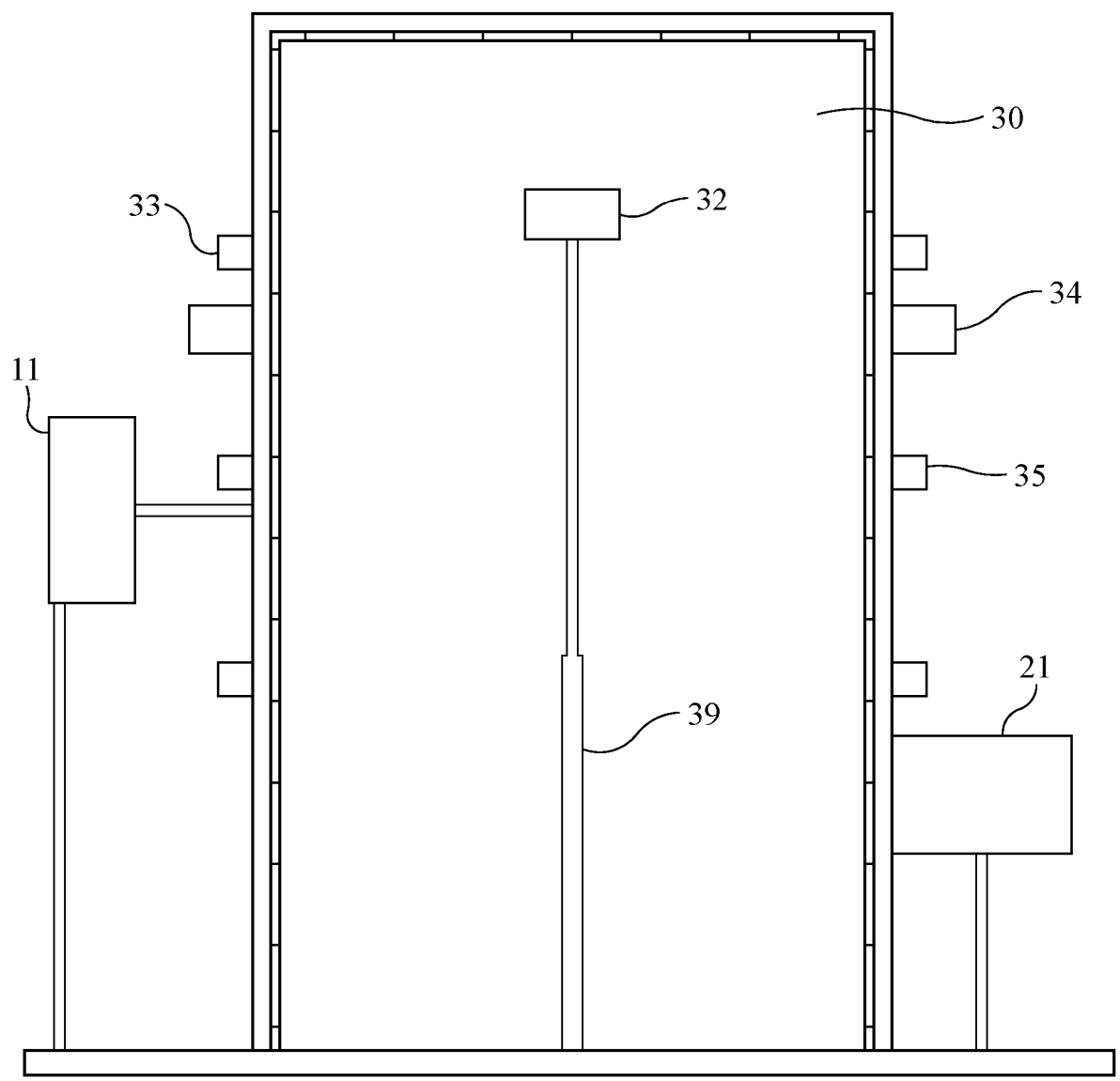
FIG. 5 is a line drawing showing the layout of a screen panel for use in a portal.

FIG. 5 shows a specific embodiment of a single screen for use in a portal, wherein a camera 32 is arranged centrally behind the screen on an adjustable, telescoping pole 39, with speakers 34, lights 35 and microphones 33 arranged along the rim of the screen. The projector 11 is located behind and to the left of the screen 30 and the sensor box 22 or cabinet 40 is located to the and in front of the screen 30.

Figure 6:
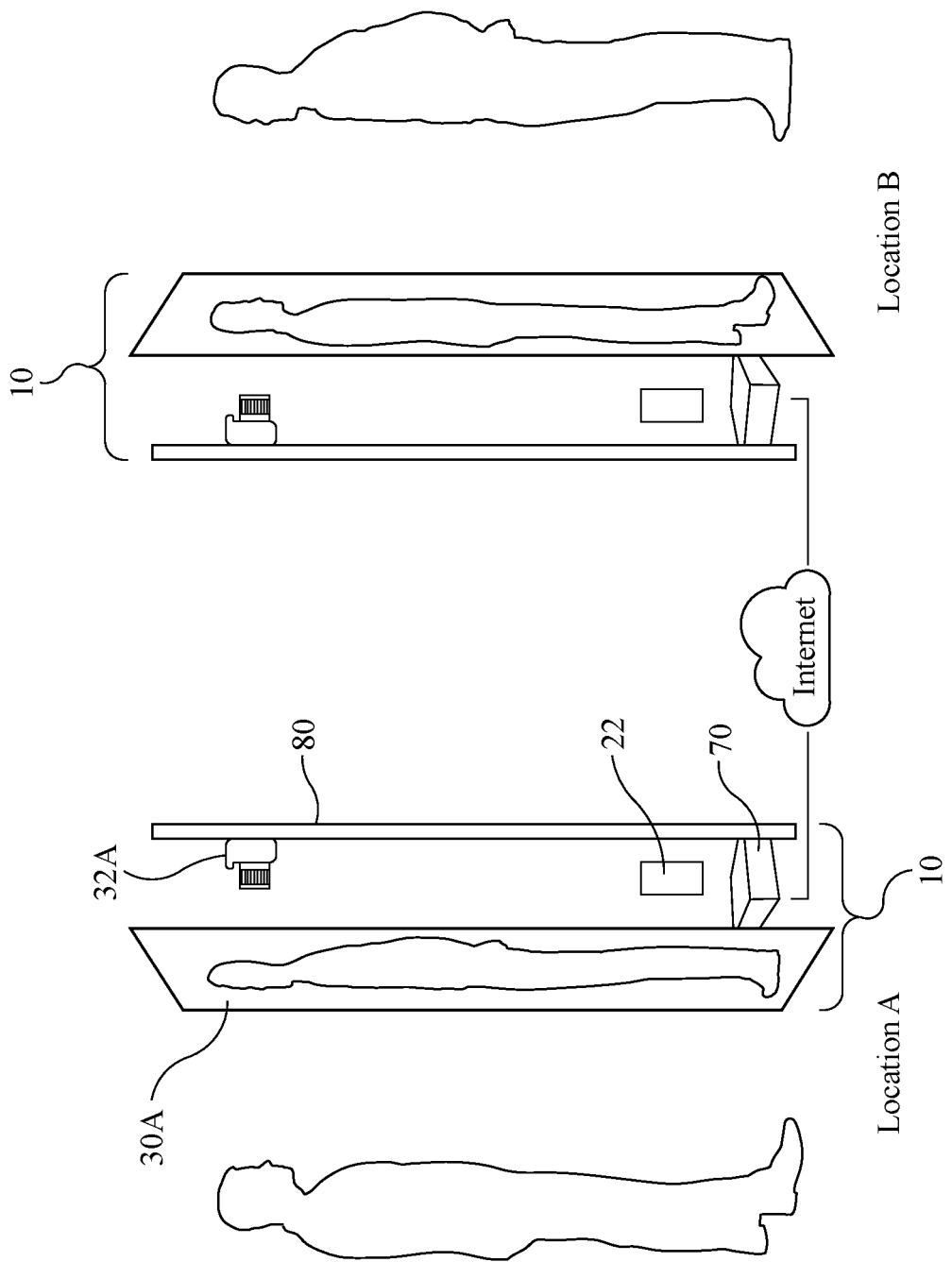
FIG. 6 is a line drawing of an alternate portal configuration employing 4K transparent LCD screens.

FIG. 6 shows an alternate iteration of two communicating portals 10, comprising a location A for a patient and location B for a health care professional, with each portal comprising at least a LCD 4K display screen 30A, preferably of the transparent variety. On a gear rack 80 behind the screen are arranged each of a UHD camera 32A and bluetooth sensor 22 to receive biometric data wirelessly from sensors 20 (not pictured), along with a CPU 70 to process and record such data.

Figure 7:
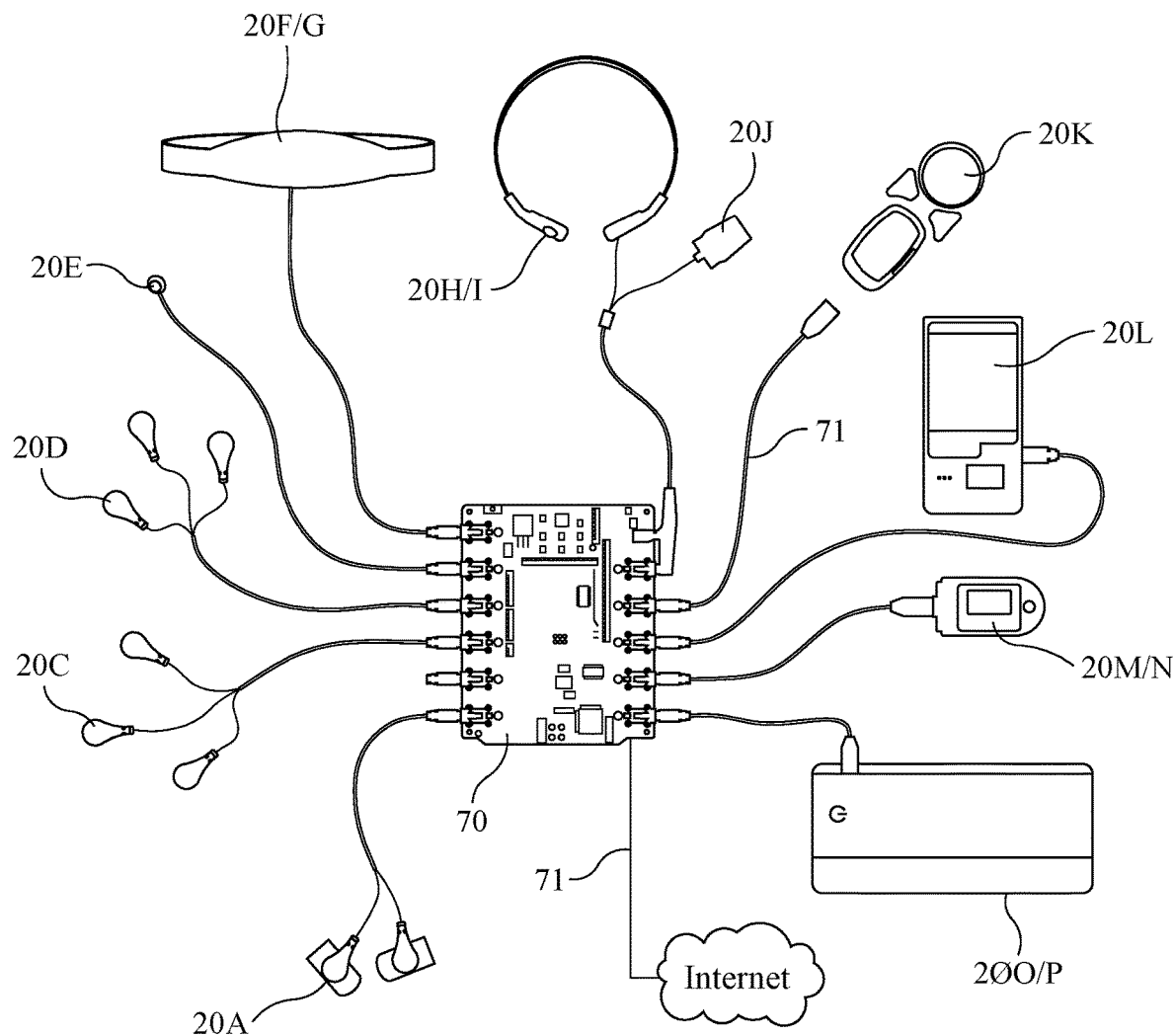
FIG. 7 is a line drawing showing an array of sensors connected to a central processor.

FIG. 7 labels certain of the biometric sensor 20 alternatives for a subject portal 10, and shows each such sensor attached by wire 71 to a CPU 70 for biometric data processing and recording. Such CPU is also connected to the internet, either by wire or any known wireless connection system, whereby such gathered and/or processed data may be communicated to one or more other portals. Such CPU-internet connection may also comprise telecommunication security protocols, including but not limited to Virtual Private Network protocols such as WireGuard® and embedded computer systems controlled by real-time operating systems (RTOS), or other comparable security features.

Figure 8:
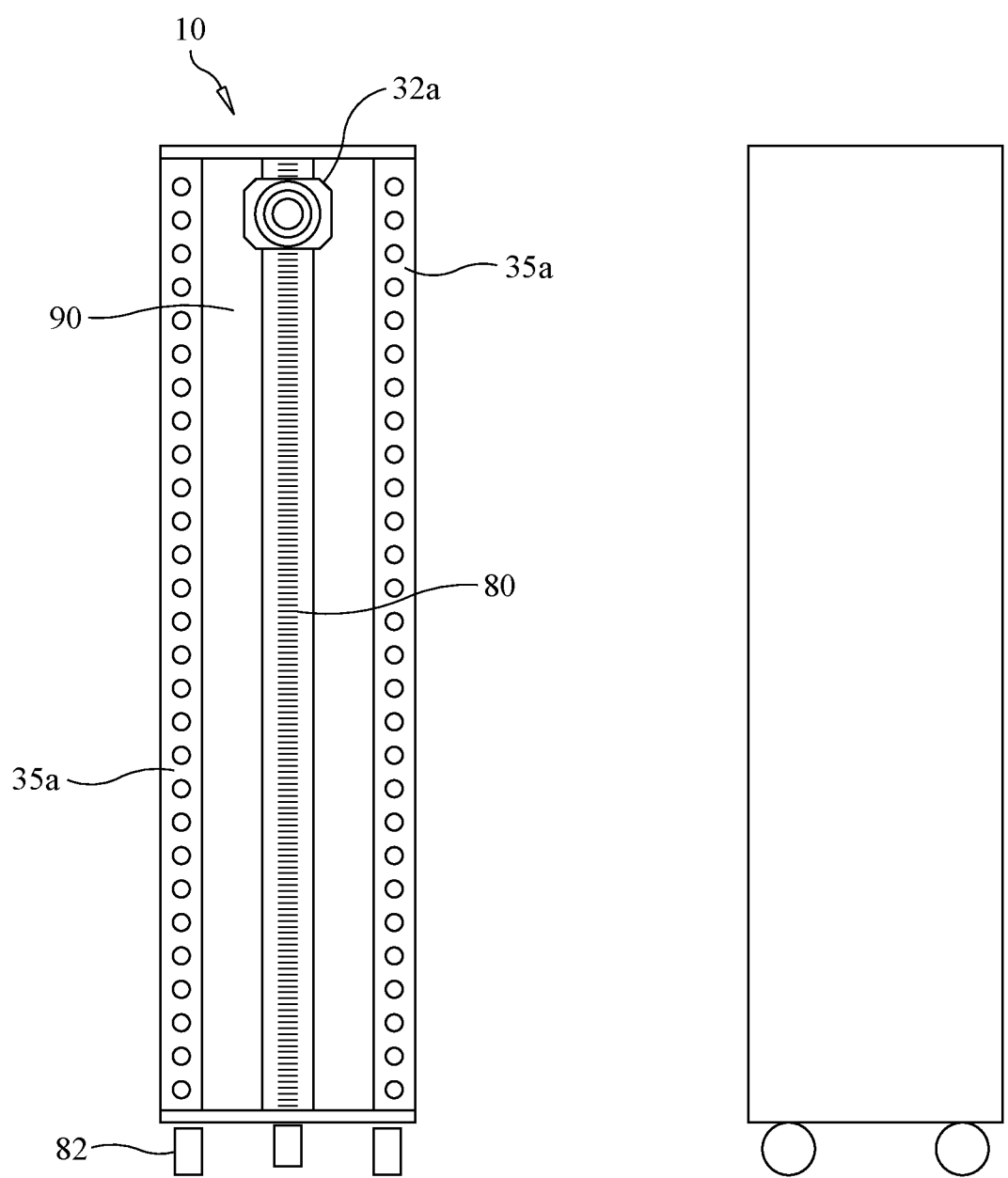
FIG. 8 is a line drawing of two views of a simplified examination portal for patients.

FIG. 8 shows an alternate embodiment of examination portal 10, wherein the portal is of a limited size and is portable. The portal 10 is encased in acrylic walls 90, with at least the front wall being transparent. Within the acrylic walls are located a Bluetooth sensor 22 for receiving signals from sensors, a gear rack 80 comprising a mount for a UHD camera 32A, as well as one or more height adjusting motors 81 and any necessary counterweights for adjusting the camera up and down, either automatically or manually, to properly match the user's height. LED light strips 35A will border either side of the front acrylic panel 90 to illuminate the user, and a plurality of retractable wheels 82, preferably embodied as casters will be located at the bottom. Such portable portals can easily be rolled from room to room, allowing for ease of patient use, but could also prove useful as a home unit for physicians.

Figure 9:
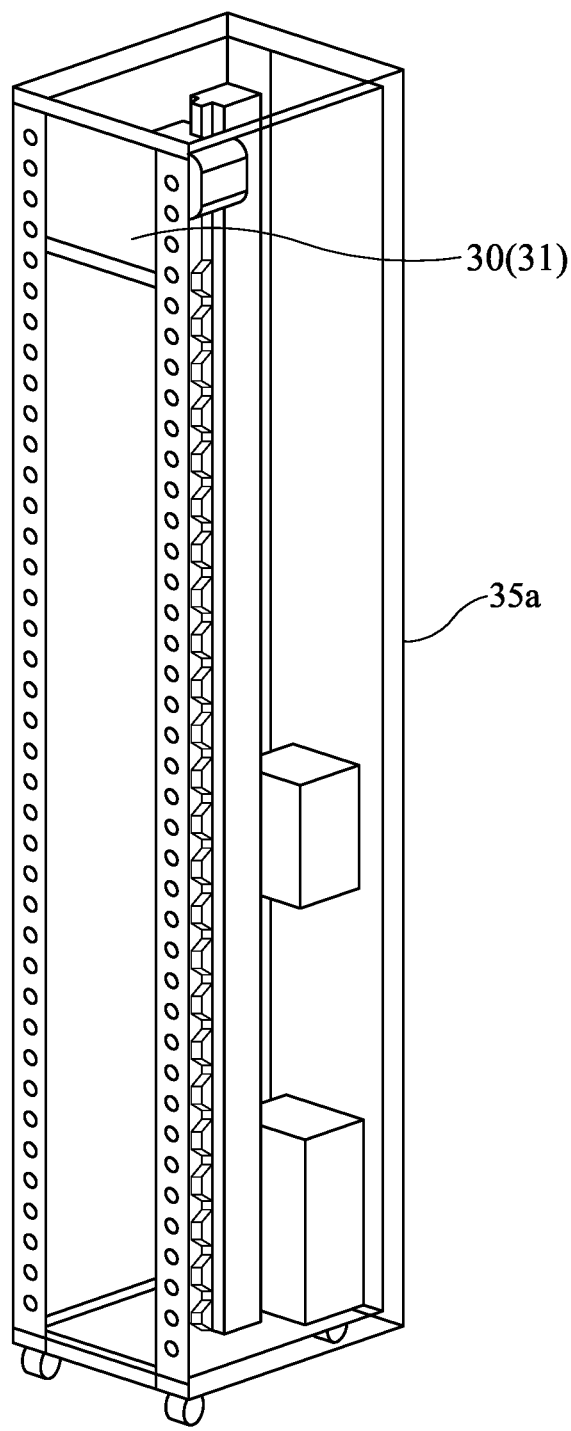
FIG. 9 is a line drawing evidencing another embodiment of the examination portal of FIG. 8, wherein a video screen has been added to the upper front of such portal.

FIG. 9 shows another embodiment of examination portal 10, wherein a video screen 30 has been added to the upper front of such portal. In practice, the screen will show a data overlay 31 providing real-time information such as the patient's vital signs, and will also comprise a conferencing capability by alternately or concurrently showing the image of the medical professional conducting the examination.

Figure 10:
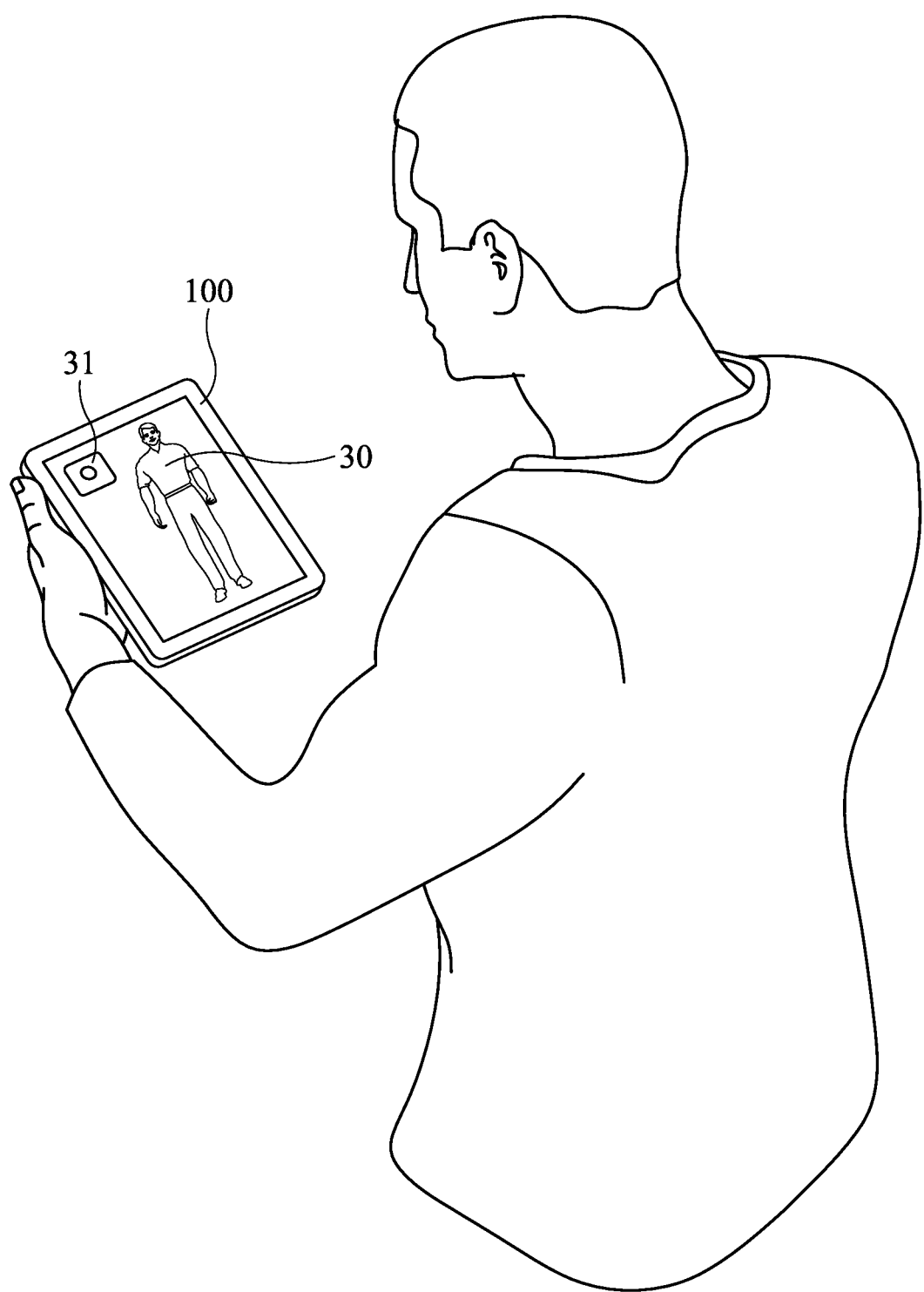
FIG. 10 is a line drawing evidencing a medical professional conducting a physical examination using a mobile device only.

FIG. 10 shows an alternate embodiment wherein the second portal of the previous iteration is replaced with a mobile device 100 with a screen 30, showing a medical professional conducting a physical examination using such mobile device with the patient appearing on the screen with a screen data overlay 31. For the purposes of this disclosure, the term "mobile device" shall mean any known mobile communication device including smart phones, tablets, smart screens, laptops, desktops, smart watches, smart glasses and all related devices.

LIST OF PARTS

10 Examination portal
11 Projector
12 Electronics box
20 Sensors
20A GSR sensor
20B Airflow sensor
20C ECG sensor
20D EMG sensor
20E Thermometer
20F Body position sensor
20G Snore sensor
20H Sound sensor
20I Sound generator
20J Alert patient button
20K Spirometer
20L Glucometer
20M SPO2 plusioximeter
20N SPO2 plusioximeter BLE
20O SPO2 Blood pressure sensor
20P SPO2 Blood pressure sensor BL
20Q Scale
20R Alarm button
20S Thermal imaging to determine body temperature and/or sites of infection
21T Stethoscope, otoscope, opthalmoscope, nasal speculum,
21U Tonometer
22V Slit lamp
22W Ophthalmoscope
22X Reflex hammer
22Y Tongue depressor
21 Sensor box
22 Bluetooth sensor
30 Screen
30A LCD 4K display screen
31 Screen data overlay
32 Camera
32A UHD camera
33 Microphone
34 Speakers
35 Lights
35A LED light strip
36 Projector
37 Frame
38 LED lights
39 Telescope
40 Cabinet
41 UVC lamps
42 Compartments
50 Mister
51 Mister reservoir
52 Mister pump
60 Ozone generator
70 Control unit or CPU
71 Wires
80 Gear rack
81 Height adjusting motors
82 Retractable wheels
90 Acrylic panel
100 Mobile device The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable equivalents.

I claim:

1. A remote communication portal system for two or more participants, comprising an examination portal connected to a mobile device by an intranet or the internet, each such portal comprising at least one of each of a video screen, a microphone, a camera, and an audio speaker, wherein the examination portal comprises one or more sensors and/or measurement devices for the gathering of biometric data, a control unit or central processor unit with a memory and power supply for the gathering and transmission of video, audio and sensor data between the examination portal and mobile device, and the mobile device comprises a means for reviewing and controlling such video, audio and sensor data, wherein the examination portal comprises an automatic biosantiation cleaning feature, such biosanitation feature comprising an ozone generator or a misting system including one or more misters, a reservoir and pump(s).

2. The system of claim 1, wherein the sensors and/or measurement devices include, without limitation, one or more of the following:
   1. GSR Sensor—Galvanic Skin Response, used to measure the electrical conductance of the skin,
   2. Airflow Sensor—Used to measure the breathing rate in a patient,
   3. ECG Sensor—Electrocardiography, used to assess the electrical and muscular functions of the heart,
   4. EMG Sensor—Electromyography, used to measure the electrical activity of muscles,
   5. Temperature Sensor—Used to monitor a patient's skin surface temperature,
   6. Body Position Sensor—Used to diagnose sleep-disordered breathing,
   7. Snore Sensor—This sensor attaches to the neck and records vibration
   8. Sound Generator
   9. Alert Patient Button
   10. Spirometer—Used to measure the volume of air inspired and expired by the lungs,
   11. Glucometer Meter—Used to check blood sugar levels,
   12. SPO2 Pulsioximeter—Used to measure oxygen levels of the blood
   13. SPO2 Pulsioximeter BLE—Used to measure oxygen levels of the blood
   14. Blood Pressure Sensor (sphygmomanometer)
   15. Blood Pressure BLE
   16. Scale
   17. Alarm Button
   18. Thermal imaging to determine body temperature and/or sites of infection 19. Stethoscope, otoscope, opthalmoscope, nasal speculum,
20. Weight scale and height measuring sensor
21. Tonometer
22. Slit lamp
23. Ophthalmoscope
24. Thermometer
25. Reflex hammer
26. Tongue depressor.

3. The system of claim 1, wherein the examination portal is used by a medical patient and the mobile device is used by a medical professional.

4. The system of claim 1, wherein the examination portal comprises one or more cabinets for storing sensors and/or measurement devices, each such cabinet comprising a UVC lamp for sanitizing such sensors and/or measurement devices.

5. The system of claim 1, further comprising one or more telecommunication security protocols, including but not limited to Virtual Private Network protocols such as Wire-Guard® and embedded computer systems controlled by real-time operating systems (RTOS), or other comparable security features.

6. The system of claim 1, further comprising one or more telecommunication-related algorithms or software such as high-efficiency video coding (HEVC), open-source software such as Arch Linux, a network control protocol such as Real Time Streaming Protocol (RTSP), Screen Overlay for displaying sensor and measurement readings or other data generated for concurrent review by one or more parties to a communication, and, optionally, onsite radio communications such as Bluetooth, BLE Bluetooth Low Energy, WiFi, or similar types of transmission technology for connectivity of sensors and measuring devices.

7. The system of claim 1, wherein the sensor and/or measurement devices are taken from the group comprising: a CT scan, ultrasound, MRI, PET scan or x-ray machine, or similar radiological device.

8. The system of claim 1, wherein the data collected by the sensor and/or measurement devices in the examination portal are visible on the mobile device by means of a screen overlay.

9. The medical examination portal as disclosed in claim 1.

10. The medical examination portal of claim 1, wherein the portal is self-contained inside an acrylic or similarly durable and transparent box, with at least one LED light strip located on the front of the transparent box and a plurality of wheels on the bottom of such box, wherein such box contains a Bluetooth sensor connected to one or more medical sensors, a motorized, adjustable gear rack comprising at least one camera and a CPU.

11. The medical examination portal of claim 1, further comprising a video screen showing a medical patient a data overlay and/or image of a medical professional examining the patient.

12. A method of conducting a medical examination on a human patient utilizing the remote communication portal system of claim 1.

13. The method of claim 12, wherein the mobile device comprises software employing a control means, whereby the medical professional may manipulate the camera, lights and microphone in the examination portal in real time via radio buttons or similar control means.

14. The method of claim 12, wherein the medical professional may use the control means to manipulate the sensors and/or measurement devices in the examination portal in real time via radio buttons, voice activation, automation in combination with commercially available artificial intelligence plugins or similar control means.

* * * * *